United States Patent [19]

Pandur

[11] 3,972,666
[45] Aug. 3, 1976

[54] APPARATUS FOR EXTRUDING DRY POWDERED MATERIALS

[75] Inventor: Stefan S. Pandur, Port Jervis, N.Y.

[73] Assignee: Kolmar Laboratories, Inc., Port Jervis, N.Y.

[22] Filed: Dec. 9, 1974

[21] Appl. No.: 530,595

[52] U.S. Cl.................................. 425/208; 425/142; 425/311; 425/377; 425/461; 264/148
[51] Int. Cl.².......................................... B29F 3/06
[58] Field of Search ............ 264/148, 151; 259/191, 259/192; 425/142, 202, 205, 208, 302, 315, 316, 311, 313, 817 R, 79, 404, 376, 377, 461, 378, 444, 131.1

[56] References Cited
UNITED STATES PATENTS

| | | | |
|---|---|---|---|
| 1,054,464 | 2/1913 | Soucek | 425/378 |
| 2,627,089 | 2/1953 | Norwood | 425/208 X |
| 3,063,361 | 11/1962 | Gehrke | 425/202 X |
| 3,128,500 | 4/1964 | Cunningham | 425/142 X |
| 3,230,902 | 1/1966 | Grimm et al. | 425/208 |
| 3,278,986 | 10/1966 | Welt | 425/378 |
| 3,366,368 | 1/1968 | Hibbing | 425/444 X |
| 3,806,291 | 4/1974 | Hendrey | 425/817 R X |

FOREIGN PATENTS OR APPLICATIONS

| | | | |
|---|---|---|---|
| 1,090,103 | 10/1954 | France | 425/205 |

Primary Examiner—Francis S. Husar
Assistant Examiner—Mark Rosenbaum
Attorney, Agent, or Firm—Andrus, Sceales, Starke & Sawall

[57] ABSTRACT

An apparatus for extruding dry powdered materials into stick form. The apparatus comprises a housing which contains a rotatable auger that conveys and extrudes the powdered material through an outlet orifice. The auger is composed of a pair of helical flight sections with the downstream flight section having a smaller pitch than the upstream flight section. The powdered material is fed to the upstream flight section through an inlet feed conduit and is extruded through the outlet orifice which is located adjacent the end of the downstream flight section and disposed generally transverse to the axis of the auger. The extruded powder rod is cut into short lengths which are conveyed to a collection area.

3 Claims, 4 Drawing Figures

U.S. Patent   Aug. 3, 1976   Sheet 1 of 2   3,972,666
*Fig. 1*
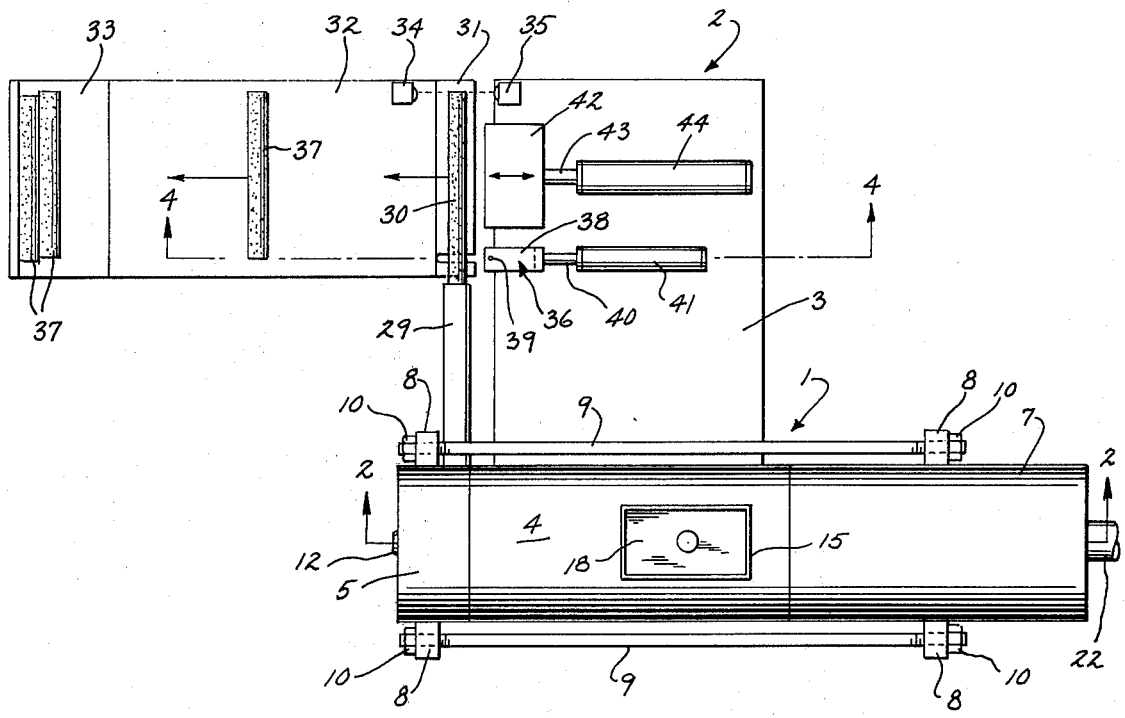
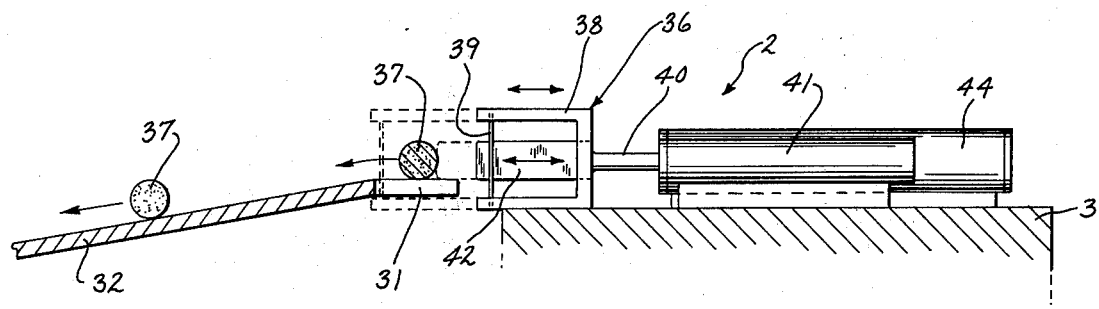
*Fig. 4*

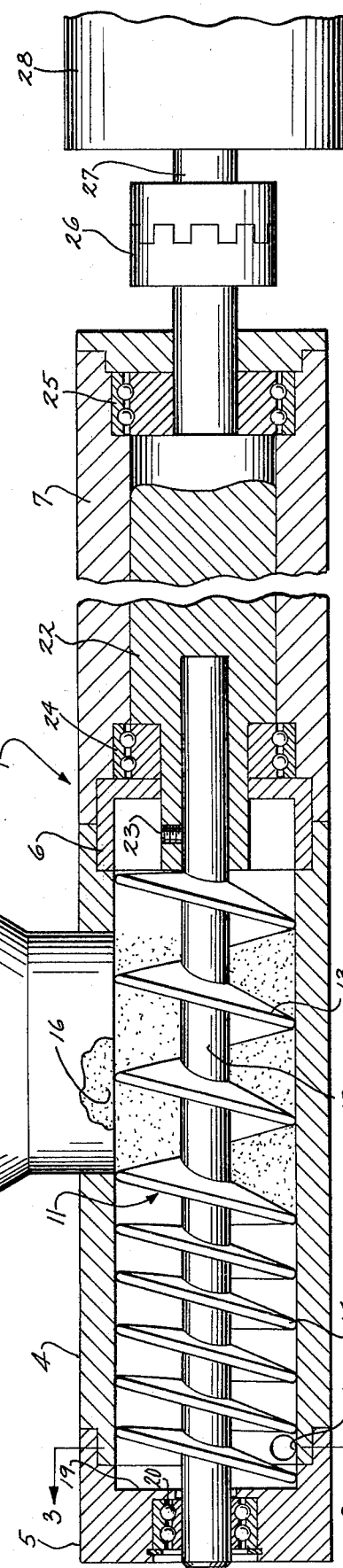

APPARATUS FOR EXTRUDING DRY POWDERED MATERIALS

BACKGROUND OF THE INVENTION

In the past, facial makeup compositions have taken the form of grease sticks, creams, or pressed powder cakes. More recently dry, pressed powder makeup sticks have been developed. The pressed powder sticks provide a matte, non-greasy finish on the skin which will not smear as do grease sticks or creams. As a further advantage, the pressed powder stick can be applied directly to the skin without the use of brushes, puffs, or the like.

A pressed powder stick cannot be satisfactorily prepared by conventional molding techniques due to the fact that the powder composition is relatively dry and contains generally less than 35% by weight of water. This dry powdered mixture lacks sufficient fluidity to enable the powder to be molded by standard processes. Incorporating additional water with the powdered mixture to improve the fluidity is not feasible, as the evaporation of the water, after molding of the sticks, leaves voids in the structure.

Pressed powder sticks have been prepared in the past by extrusion methods. However, the use of standard extrusion apparatus has not proven entirely successful, because of the relatively dry and abrasive nature of the powder composition. It has been found that employing a hydraulic extrusion apparatus, in which a hydraulic ram is used to extrude the powder mixture through an axial orifice, will result in the water being squeezed from the powder mixture. Squeezing the water from the powder mixture further reduces the fluidity of the powder and increases the frictional resistance of the mass, thereby generating heat and evaporating additional water from the powder mixture to compound the problem. Thus, in the past, pressed powder sticks have not been successfully extruded on a commercial scale due to the dry and abrasive nature of the powder mixture.

SUMMARY OF THE INVENTION

The present invention relates to an apparatus for extruding dry powdered material into stick form. The apparatus comprises a generally cylindrical housing which contains a rotatable auger that is adapted to convey and extrude the powdered material. The auger is composed of a pair of helical flight sections, with the downstream flight section having a smaller pitch than the upstream flight section.

The downstream end of the housing is enclosed by an end wall which is disposed generally normal to the axis of the auger, and the end of the downstream flight section terminates adjacent the end wall. Located in the cylindrical housing adjacent the end wall is an outlet orifice that is disposed generally transverse to the axis of the auger.

The powdered material is fed into the housing through an inlet feed conduit that communicates with the upstream flight section and is extruded by the downstream flight section through the outlet orifice in the form of a rod.

The extruded powdered rod being discharged from the housing is cut into short lengths by a cutting mechanism and conveyed to a collection area.

Through use of the apparatus of the invention, low moisture, highly abrasive powdered materials can be extruded into rod or stick form. The use of the dual pitched auger in conjunction with the transverse outlet orifice provides a uniform mixing of the materials and prevents the buildup of high pressures which ordinarily accompany the extrusion of dry abrasive materials in conventional hydraulic extrusion devices.

Other objects and advantages will appear in the course of the following description.

DESCRIPTION OF THE DRAWINGS

The drawings illustrate the best mode presently contemplated of carrying out the invention.

In the drawings:

FIG. 1 is a top plan view of the apparatus of the invention;

FIG. 2 is a longitudinal section of the extruding apparatus;

FIG. 3 is a section taken along line 3—3 of FIG. 3; and

FIG. 4 is a view taken along line 4—4 of FIG. 1;

DESCRIPTION OF THE PREFERRED EMBODIMENT

The drawings illustrate an apparatus for forming relatively dry powdered materials into stick form which includes an extruding unit 1 and a cut-off mechanism 2, which are mounted on a supporting surface of foundation 3.

The extruding unit 1 includes a generally cylindrical housing 4, and the ends of the housing are enclosed by heads 5 and 6. A cylindrical bearing housing 7 forms an extension to the housing 4 and is provided with a flange which is located around the head 6.

To secure the members together, a series of lugs 8 are secured to the head 5 and to the bearing housing 7, and the lugs 8 are provided with openings which receive tie rods 9. Nuts 10 are threaded onto the ends of the tie rods 9 to clamp the members together.

Located within the housing 4 is an auger 11 composed of a central shaft 12 and a pair of spiral or helical flight sections 13 and 14. The flight section 14 is located in a downstream direction with respect to the conveying action of the auger, and the flight section 14 has a lesser pitch than flight section 13. As shown in the drawings, the pitch of the downstream flight section 14 is about one-half of the pitch of the upstream flight section 13.

A dry powdered material is adapted to be introduced into the upstream end of the housing 4 through a hopper 15 which communicates with an opening 16 in the housing 4. The powdered material 17 can be a relatively dry, abrasive mixture of cosmetically compatible materials, such as that disclosed in U.S. Pat. No. 3,800,034. The dry blend of materials is mixed with a liquid carrier, such as water and, in general, the powder mixture contains from about 20% to 35% by weight of water, with the result that the individual particles or grains of the powdered materials are combined in the form of small, relatively uniformly sized, agglomerates or balls which are moist to the touch.

To aid in moving the powdered material 17 downwardly into the housing 4, a pressure plate 18 can be disposed within the hopper. Manual downward pressure on the pressure plate will serve to force the powdered material 17 into the housing 4 where it is conveyed by the upstream flight section 13 toward the head 5.

As best shown in FIG. 2, the end of the downstream flight section 14 terminates immediately adjacent the surface 19 of head 5, and the surface 19 is generally normal to the axis of the shaft 12. The end of the shaft 12 is journalled within a bearing assembly 20 located in the head 5.

The spiral flight section 13 of the auger serves to convey the powdered material 17 toward the head 5, and the flight section 14, having a lesser pitch, acts to mix or knead the powdered composition to provide the desired consistency for proper extrusion. The powdered mixture is extruded from the housing 4 through an outlet orifice 21 located adjacent the end of the flight section 14. Outlet orifice 21 extends generally transverse of the axis of the auger shaft 12. The use of the outlet orifice, which is located at an angle to the axis of the auger, is an important feature of the invention in that the material can be extruded through the orifice 21 without the buildup of excessive pressure as accompanies an axial type of extrusion.

To drive the auger 11, the end of the auger shaft 12 is secured within an axial bore in a shaft 22 by a set screw 23 and the shaft 22 is journalled within the bearing housing 7 by a pair of bearing assemblies 24 and 25. The opposite end of the shaft 22 is attached through a coupling 26 to the output shaft 27 of a variable speed motor 28. With this construction, operation of the motor 28 will act to drive the auger to thereby move the powdered material toward the head 5 and extrude the material through the transverse outlet orifice 21.

Connected to the outlet orifice 21 is a nozzle or tube 29 and a continuous rod 30 of the extruded powdered material is discharged from the nozzle 29 onto a tray 31. An inclined ramp 32 slopes downwardly from the tray 31 and leads to a collection area 33.

The end of the extruded rod 30 is sensed by a pair of photoelectric eyes 34 and 35 which are mounted adjacent the end of the tray 31. As the end of the extruded rod 30 advances, it breaks the beam between the photoelectric eyes 34 and 35, and a cutting mechanism 36 is actuated to cut the end portion of the rod 30 into a short stick, as shown by 37. The cutting mechanism, as illustrated in the drawings, includes a U-shaped bracket 38 having a cutting wire 39 which extends across the free ends of the bracket. The bracket 38 is moved toward and away from the extruded rod 30 by an air-cylinder unit including a ram 40 which is attached to the bracket 38 and is slidable within a cylinder 41. Outward movement of the ram 40 will cause the cutting wire 39 to cut or sever the end portion of the rod 30 into the stick 37. While the drawings illustrate the cutting mechanism in the form of a wire, it is contemplated that other cutting mechanisms, such as knives or saws can be substituted.

After the stick 37 is cut from the extruded rod 30, the stick is pushed down the inclined ramp 32 by a pusher block 42. Block 42 is connected to a ram 43 of an air cylinder 44, and after the cutting wire 39 has cut the extruded rod and returned to its original position, the ram 43 is extended, moving the block 42 outwardly to push the cut stick 37 down the incline to the collection area 33. The sticks are then dried slowly to equilibrium conditions with the atmosphere.

The apparatus of the invention enables low moisture, highly abrasive powdered materials to be extruded into rod form which is then cut into a series of short sticks. The combination of the dual-flight auger along with the lateral outlet orifice produces proper kneading of the powdered material without separation of the water or moisture to enable the powdered material to be extruded without generating excessive pressure or temperatures which could result in the evaporation of moisture to increase the frictional resistance and compound the pressure and temperature build-up.

It is contemplated that the apparatus can be used to extrude various types of powdered or granular materials, and particularly those materials having a low-moisture content and abrasive characteristics, into a variety of diameters, lengths and shapes. The apparatus has use in extruding cosmetic make-up sticks, such as eye shadow sticks, face makeup sticks and eyebrow sticks, as well as drug products in stock form, such as anti-perspirant and deodorant sticks.

Various modes of carrying out the invention are contemplated as being within the scope of the following claims particularly pointing out and distinctly claiming the subject matter which is regarded as the invention.

I claim:

1. An apparatus for extruding dry powdered materials, comprising a housing having a generally cylindrical internal chamber, an auger disposed within the chamber and having a first spiral flight section and a second spiral flight section located axially of said first section, drive means connected to said auger for rotating the auger in a direction whereby material is conveyed from said first flight section toward said second flight section, inlet feed means communicating with the chamber for delivering powdered material to the first flight section, and outlet means communicating with the chamber at the location of the second flight section, said outlet means including an outlet passage disposed generally transverse to the axis of said auger, and extending generally tangentially of said cylindrical chamber, said powdered material being conveyed by said first flight section to said second flight section and said second flight section extruding said material through said outlet passage to the exterior.

2. The apparatus of claim 1, wherein said housing has an end wall disposed generally normal to the axis of the auger, an end of said second flight section terminating adjacent said end wall.

3. The apparatus of claim 2, wherein said outlet passage is disposed adjacent said end of the second flight section.

* * * * *